(12) United States Patent
Shimura et al.

(10) Patent No.: US 10,431,825 B2
(45) Date of Patent: Oct. 1, 2019

(54) NEGATIVE ELECTRODE FOR SECONDARY BATTERY, METHOD FOR MANUFACTURING SAME, AND SECONDARY BATTERY USING SAME

(71) Applicant: NEC Corporation, Minato-ku, Tokyo (JP)

(72) Inventors: Midori Shimura, Tokyo (JP); Noriyuki Tamura, Tokyo (JP); Kentaro Nakahara, Tokyo (JP)

(73) Assignee: NEC CORPORATION, Tokyo (JP)

( * ) Notice: Subject to any disclaimer, the term of this patent is extended or adjusted under 35 U.S.C. 154(b) by 305 days.

(21) Appl. No.: 14/909,185

(22) PCT Filed: Aug. 4, 2014

(86) PCT No.: PCT/JP2014/070526
§ 371 (c)(1),
(2) Date: Feb. 1, 2016

(87) PCT Pub. No.: WO2015/020013
PCT Pub. Date: Feb. 12, 2015

(65) Prior Publication Data
US 2016/0172677 A1     Jun. 16, 2016

(30) Foreign Application Priority Data

Aug. 8, 2013   (JP) .................................. 2013-165385

(51) Int. Cl.
*H01M 4/62* (2006.01)
*C07D 305/06* (2006.01)
(Continued)

(52) U.S. Cl.
CPC ............ *H01M 4/62* (2013.01); *C07D 305/00* (2013.01); *C07D 305/06* (2013.01);
(Continued)

(58) Field of Classification Search
None
See application file for complete search history.

(56) References Cited

U.S. PATENT DOCUMENTS

| 7,285,334 B1* | 10/2007 | Yamashita | ........... H01M 2/0267 428/220 |
| 2006/0147809 A1* | 7/2006 | Amine | .............. H01M 10/0567 429/326 |

(Continued)

FOREIGN PATENT DOCUMENTS

| JP | 2001-155767 A | 6/2001 |
| JP | 2003-016835 A | 1/2003 |

(Continued)

OTHER PUBLICATIONS

Nomura JP2015028866A Machine translation (Year: 2015).*

(Continued)

*Primary Examiner* — Ula C Ruddock
*Assistant Examiner* — Anna Korovina

(57) ABSTRACT

The present invention relates to a negative electrode for a lithium ion secondary battery comprising an oxetane compound represented by a predetermined formula in an amount within a range of 0.001% by mass or more and 5.0% by mass or less based on the amount of a negative electrode active material, and a lithium ion secondary battery using the same.

9 Claims, 1 Drawing Sheet

(51) Int. Cl.
*H01M 4/13* (2010.01)
*H01M 10/0525* (2010.01)
*H01M 4/04* (2006.01)
*H01M 4/139* (2010.01)
*H01M 4/02* (2006.01)
*C07D 305/00* (2006.01)
*H01M 4/1393* (2010.01)

(52) U.S. Cl.
CPC ........... *H01M 4/0404* (2013.01); *H01M 4/13* (2013.01); *H01M 4/139* (2013.01); *H01M 10/0525* (2013.01); *H01M 4/1393* (2013.01); *H01M 2004/027* (2013.01); *H01M 2220/20* (2013.01); *H01M 2220/30* (2013.01); *Y02E 60/122* (2013.01); *Y02P 70/54* (2015.11); *Y02T 10/7011* (2013.01)

(56) References Cited

U.S. PATENT DOCUMENTS

2011/0294003 A1　12/2011　Zhang et al.
2013/0260207 A1*　10/2013　Uemura .................. H01M 2/16
　　　　　　　　　　　　　　　　　429/144

FOREIGN PATENT DOCUMENTS

| JP | 2005-332606 | A | | 12/2005 |
| JP | 2007-005314 | A | | 1/2007 |
| JP | 2010-199043 | A | | 9/2010 |
| JP | 2013530944 | A | | 8/2013 |
| JP | 2015028866 | A | * | 2/2015 |

OTHER PUBLICATIONS

Hamamoto JP2001155767A Machine Translation (Year: 2001).*
Tsurumaki Shigeru JP2010199043A Machine Translation (Year: 2010).*
International Search Report for PCT Application No. PCT/JP2014/070526, dated Sep. 22, 2014.
Japanese Office Action for JP Application No. 2015-530887 dated Jul. 10, 2018 with English Translation.

* cited by examiner

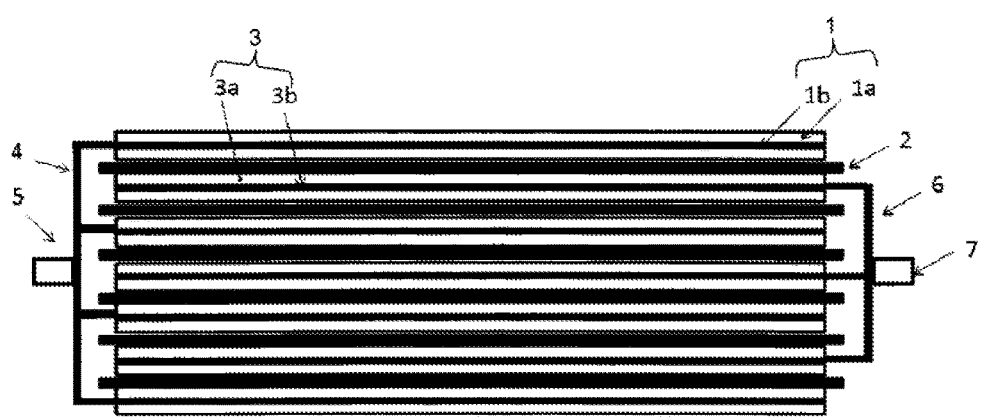

NEGATIVE ELECTRODE FOR SECONDARY BATTERY, METHOD FOR MANUFACTURING SAME, AND SECONDARY BATTERY USING SAME

This application is a National Stage Entry of PCT/JP2014/070526 filed on Aug. 4, 2014, which claims priority from Japanese Patent Application 2013-165385 filed on Aug. 8, 2013, the contents of all of which are incorporated herein by reference, in their entirety.

TECHNICAL FIELD

The present invention relates to a nonaqueous electrolyte solution secondary battery, specifically a lithium ion secondary battery, and in particular a negative electrode which can improve battery characteristics.

BACKGROUND ART

Nonaqueous electrolyte solution lithium ion batteries or lithium secondary batteries comprising a carbon material, an oxide, a lithium alloy or a lithium metal as a negative electrode, and a lithium-containing transition metal complex oxide as a positive electrode, and further comprising an electrolyte solution containing a chain or cyclic carbonate solvent, have attracted attention as power supplies for cellular phones, laptop computers or the like because they can achieve a high energy density. Recently, they have attracted attention also as power supplies for motor drive in hybrid electric vehicles (HEV) or the like because of the improvement of output characteristics and long-term reliability such as a storage characteristic.

In these secondary batteries, it is known that, for purpose of suppressing a reaction between the surface of negative electrodes and the solvent molecule, additives are added to the electrolyte solution to form a film called protective coating (or coating, SEI) derived from the additives on the surface of the negative electrodes utilizing an electrochemical reaction in a charge/discharge process, thereby improving the basic characteristics and reliability of the secondary battery. The coating significantly affects charge/discharge efficiency, cycle lifetime and safety, and therefore it is known that the formation and control of the coating on the surface of negative electrodes is essential in order to achieve a battery with a high performance. Although a secondary battery using a coating-forming additive for an electrolyte solution exhibits very excellent battery characteristics, the secondary battery had problems as follows.

When a coating-forming additive is added to an electrolyte solution, the electrolyte solution contacts not only with a negative electrode, but also with a positive electrode, and therefore a decomposition product of the additive is generated due to oxidation decomposition on the surface of the positive electrode. The decomposition product of the additive is eluted in the electrolyte solution to cause the increase of the viscosity and the reduction of the ion conductivity of the electrolyte solution, which deteriorates the battery characteristics. In addition, also after the formation of a coating in a charge/discharge process, the additive in the electrolyte solution is not completely consumed and a part thereof remains, and therefore repeated charging/discharging grows a new coating to cause the increase of the internal resistance of the negative electrode, which deteriorates the battery characteristics. Further, a coating-forming additive is generally highly reactive, and had a problem of a poor storage stability in an electrolyte solution.

On the other hand, Patent Literature 1 and Patent Literature 2 describe a method for producing an electrode by adding a coating-forming additive in a negative electrode slurry.

CITATION LIST

Patent Literature

Patent Literature 1: Japanese Patent Laid-Open No. 2010-199043
Patent Literature 2: Japanese Patent Laid-Open No. 2005-332606

SUMMARY OF INVENTION

Technical Problem

As described in Patent Literatures 1 and 2, in the case that a negative electrode slurry contains an additive, it is believed that the amount of the additive remaining in a nonaqueous electrolyte solution can be reduced after the formation of a coating by the additive, but, depending on the amount of the additive to be added, the additive is eluted into the electrolyte solution and may cause the above-described deterioration of battery characteristics. Further, depending on the amount of the additive to be added, the dispersed state of the slurry is altered to cause the slurry to clump or separate and make the slurry ununiform during the slurry production, which makes preparation of a uniform negative electrode impossible. Furthermore, a large amount of the additive attaches to the binder to reduce the binding effect and as a result deteriorates the adhesion properties between the negative electrode and the collector, leading to the shortening of cycle lifetime or capacitance degradation.

The object of the present invention is to solve the above-described problems and to provide a negative electrode which provides a lithium ion secondary battery excellent in a cycle characteristic.

Solution to Problem

The present invention relates to the following items.

A negative electrode for a lithium ion secondary battery comprising a negative electrode active material and a coating-forming additive,
wherein the negative electrode comprises the coating-forming additive in an amount within a range of 0.001% by mass or more and 5.0% by mass or less based on an amount of the negative electrode active material; and
the coating-forming additive is at least one selected from the group consisting of a compound represented by formula (1) and a compound represented by formula (2):

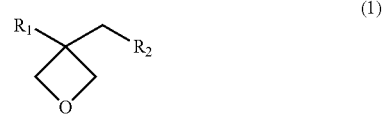

wherein
$R_1$ represents —H or alkyl group having 1 to 5 carbon atoms; and
$R_2$ represents —OH, —O—X, —O—C(=O)X, —O—C(=O)—O—X, —O—C(=O)—NH—X, —O—P(=O)(OC$_a$H$_{2a+1}$)$_2$, —O—P(OC$_b$H$_{2b+1}$)$_2$, or —O—P(=O)(OC$_c$H$_{2c+1}$)(C$_d$H$_{2d+1}$), and wherein X represents alkyl group, alkenyl group, or phenyl group; and a, b, c and d each independently represent an integer of 1 to 10;

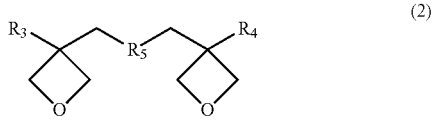

(2)

wherein $R_3$ and $R_4$ each independently represent —H, —$CH_3$, or —$C_2H_5$; and $R_5$ represents —O—, —O—Y—O—, —O—C(=O)—Y—C(=O)—O—, —O—C(=O)—NH—Y—NH—C(=O)—O—, —(O—$C_6H_4$)$_q$— (q is an integer of 1 to 5), —(O—$CH_2$—$C_6H_4$—$CH_2$)—O— (n is an integer of 1 to 5), —O—P(=O)(O$C_sH_{2s+1}$)—O— (s is an integer of 1 to 10), —O—P(O$C_mH_{2m+1}$)—O— (m is an integer of 1 to 10), —O—P(=O)($C_tH_{2t+1}$)—O— (t is an integer of 1 to 10) or —O—P(—$C_6H_5$)—O—, and wherein —Y— represents —$C_pH_{2p}$— (p is an integer of 1 to 10), cyclohexylene group, alkenylene group, —($C_6H_4$)$_r$— (r is an integer of 1 to 5), —($C_uH_{2u}$—O)$_x$— (u is an integer of 1 to 10, and x is an integer of 1 to 5), —($CH_2$—$CH_2$—O)$_k$—$CH_2$—$CH_2$— (k is an integer of 0 to 3) or —C(=O)—.

It is noted that, in this specification, the compound represented by formula (1) is sometimes referred to as "Compound (1)" and the compound represented by formula (2) as "Compound (2)". Further, the compound represented by formula (1) or formula (2) is sometimes simply referred to as "oxetane compound".

Advantageous Effect of Invention

According to the present invention, a lithium ion secondary battery excellent in a cycle characteristic with the increase of the resistance suppressed can be provided.

BRIEF DESCRIPTION OF DRAWING

FIG. 1 is a schematic cross-sectional view illustrating the structure of an electrode element used in a laminated type secondary battery.

DESCRIPTION OF EMBODIMENTS

Examples of the electrode of the present invention and a secondary battery capable of using the electrode will be described with respect to individual elements thereof.

[1] Negative Electrode

Negative Electrode Active Material Layer

A negative electrode is constituted by, for example, binding a negative electrode active material to a negative electrode collector with a negative electrode binder. As the negative electrode active material in the present embodiment, any one capable of absorbing and desorbing lithium may be used as long as it does not significantly deteriorate the effect of the present invention. A negative electrode is used having a structure in which a negative electrode active material layer is provided on a collector.

As the negative electrode active material, known negative electrode active materials may be arbitrary used as long as it is a material capable of absorbing and desorbing lithium ions, without any other limitation. For example, it is preferable to use a carbonaceous material such as natural graphite, artificial graphite, hardly-graphitizable carbon, easily-graphitizable carbon, coke, acetylene black, mesophase microbeads and graphite; lithium metal; a lithium alloy such as a lithium-silicon and a lithium-tin; and lithium titanate or the like. Among them, it is the most preferable to use a carbonaceous material from the viewpoint of its good cycle characteristic and safety and further excellent continuous charge characteristics. It is noted that one negative electrode active material may be used singly or two or more negative electrode active materials may be used in any combination and ratio.

Although the particle size of the negative electrode active material is arbitrary as long as it does not significantly deteriorate the effect of the present invention, it is usually 1 µm or more, preferably 15 µm or more, and usually 50 µm or less, preferably approximately 30 µm or less from the viewpoint of excellent battery characteristics such as initial efficiency, rate characteristics and a cycle characteristic. Further, as the carbonaceous material may be suitably used, for example, a material which is obtained by coating the above carbonaceous material with an organic substance such as pitch and thereafter burning it and a material which is obtained by forming more amorphous carbon than the above carbonaceous material on the surface by using a CVD method or the like. Here, examples of the organic substance used for coating include coal tar pitch from soft pitch to hard pitch; coal heavy oils such as dry distillation liquefaction oil; straight-run heavy oils such as atmospheric residue and vacuum residue; and petroleum heavy oils such as cracked heavy oil (e.g., ethylene heavy end), which is a byproduct generated in thermal cracking of crude oil, naphtha and the like. Also may be used a material obtained by pulverizing a solid residue obtained by distilling these heavy oils at 200 to 400° C. into 1 to 100 µm. In addition, a vinyl chloride resin, a phenol resin, an imide resin or the like may also be used. The negative electrode active material layer may be produced, for example, by roll-forming the above-mentioned negative electrode active material into a sheet electrode or compression-molding the negative electrode active material into a pellet electrode; however, usually as is the case with a positive electrode active material layer, the negative electrode active material layer may be produced by applying an application liquid obtained by slurrying the above-mentioned negative electrode active material, a binder, and as necessary various auxiliary agents or the like in a solvent to a collector and drying.

Examples of the negative electrode active material containing silicon include silicon and a silicon compound. Examples of the silicon include elemental silicon. Examples of the silicon compound include a silicon oxide, a silicate, and a compound containing a transition metal and silicon, such as nickel silicide or cobalt silicide. A silicon compound has a function to relax expansion and contraction of the negative electrode active material itself caused in repeating the charge/discharge cycle, and is preferably used from the viewpoint of the charge/discharge cycle characteristic. Besides, some types of silicon compounds have a function to secure connection between silicon portions, and from this point of view, a silicon oxide is preferably used as the silicon compound.

The silicon oxide is not especially limited, but for example, a silicon oxide is represented by $SiO_x$ ($0<x<2$). A silicon oxide may contain Li. A silicon oxide containing Li is represented by, for example, $SiLi_yO_z$ ($y>0$ and $2>z>0$). Besides, the silicon oxide may contain a slight amount of a metallic element or a nonmetallic element. The silicon oxide may contain one, two or more elements selected from the group consisting of, for example, nitrogen, boron and sulfur in a concentration of, for example, 0.1 to 5% by mass. If a slight amount of a metallic element or a nonmetallic element is contained, the electric conductivity of the silicon oxide can be improved.

The silicon oxide may be crystalline or amorphous. The negative electrode active material preferably contains, in addition to the silicon or the silicon oxide, a carbon material capable of absorbing and desorbing lithium ions. The carbon material may be contained in a state conjugated with the silicon or the silicon oxide. The carbon material has, similarly to the silicon oxide, functions to relax the expansion and contraction of the negative electrode active material itself caused in repeating the charge/discharge cycle, and to secure the connection between silicon portions of the negative electrode active material. Accordingly, if the silicon, the silicon oxide and the carbon material are used together, a better cycle characteristic can be attained.

As the carbon material, graphite, amorphous carbon, diamond-like carbon, a carbon nanotube, or a complex of these materials can be used. Here, graphite with high crystallinity has high electric conductivity and is excellent in adhesion to a negative electrode collector made of a metal such as copper and in voltage flatness. On the other hand, amorphous carbon with low crystallinity shows comparatively small volume expansion and hence attains a high effect to relax the volume expansion of the whole negative electrode, and degradation derived from ununiformity such as a grain boundary or a defect is less likely to occur therein. The content of the carbon material in the negative electrode active material is preferably 2% by mass or more and 50% by mass or less, and more preferably 2% by mass or more and 30% by mass or less.

As a method for preparing the negative electrode active material containing the silicon and the silicon compound, if, for example, a silicon oxide is used as the silicon compound, a method including mixing elemental silicon with the silicon oxide and sintering the resulting mixture at a high temperature and reduced pressure may be employed. Alternatively, if a compound containing a transition metal and silicon is used as the silicon compound, a method including mixing elemental silicon with the transition metal and fusing the resulting mixture, or a method including coating the surface of elemental silicon with the transition metal by vapor deposition or the like may be employed.

As a method for producing a negative electrode active material, in addition to any of the aforementioned preparing methods, conjugation with carbon may be employed in combination. For example, by a method including introducing a sintered product of a mixture of elemental silicon and a silicon compound into a gaseous atmosphere of an organic compound under non-oxygen atmosphere at high-temperature, or a method including mixing a sintered product of a mixture of elemental silicon and a silicon oxide with a carbon precursor resin under non-oxygen atmosphere at high-temperature, a coating layer of carbon can be formed around a nucleus of the elemental silicon and the silicon oxide. In this manner, effects to inhibit the volume expansion through the charge/discharge cycle and to further improve the cycle characteristic can be attained.

In the case that silicon is used as the negative electrode active material in the present embodiment, the negative electrode active material preferably is formed from a complex containing silicon, a silicon oxide and a carbon material (hereinafter also referred to as Si/SiO/C complex). The whole or a part of the silicon oxide preferably has an amorphous structure. A silicon oxide having an amorphous structure can inhibit the volume expansion of the carbon material or the silicon used as the other components of the negative electrode active material. This mechanism has not been clarified yet, but it is presumed that a silicon oxide having an amorphous structure somehow affects the formation of a coating on an interface between the carbon material and the electrolyte solution. Besides, it seems that an amorphous structure includes a comparatively small number of elements derived from ununiformity such as a grain boundary or a defect. Incidentally, it can be confirmed by X-ray diffraction measurement (such as general XRD measurement) that the whole or a part of the silicon oxide has an amorphous structure. Specifically, if a silicon oxide does not have an amorphous structure, a peak peculiar to the silicon oxide is observed, but if the whole or a part of the silicon oxide has an amorphous structure, the peak peculiar to the silicon oxide is observed as a broad peak.

In the Si/SiO/C complex, the whole or a part of the silicon is preferably dispersed in the silicon oxide. By dispersing at least a part of the silicon in the silicon oxide, the volume expansion of the whole negative electrode can be more inhibited, and the decomposition of the electrolyte solution can be also inhibited. Incidentally, it can be confirmed by observation with a combination of a transmission electron microscope (general TEM observation) and energy dispersive X-ray spectroscopy (general EDX measurement) that the whole or a part of the silicon is dispersed in the silicon oxide. Specifically, a cross-section of a sample is observed, and the oxygen concentration in a silicon portion dispersed in the silicon oxide is measured, so as to confirm that the silicon portion is not an oxide.

In the Si/SiO/C complex, for example, the whole or a part of the silicon oxide has an amorphous structure, and the whole or a part of the silicon is dispersed in the silicon oxide. Such a Si/SiO/C complex can be prepared by, for example, a method disclosed in Japanese Patent Laid-Open No. 2004-47404. Specifically, the Si/SiO/C complex can be obtained, for example, by subjecting a silicon oxide to a CVD treatment under an atmosphere containing an organic gas such as a methane gas. The Si/SiO/C complex obtained by this method is in such a form that surfaces of particles of the silicon oxide containing silicon are coated with carbon. Besides, the silicon is present in the form of nanoclusters in the silicon oxide.

In the Si/SiO/C complex, the ratio among the silicon, the silicon oxide and the carbon material is not especially limited. The silicon is contained in the Si/SiO/C complex in a percentage of preferably 5% by mass or more and 90% by mass or less, and more preferably 20% by mass or more and 50% by mass or less. The silicon oxide is contained in the Si/SiO/C complex in a percentage of preferably 5% by mass or more and 90% by mass or less, and more preferably 40% by mass or more and 70% by mass or less. The carbon material is contained in the Si/SiO/C complex in a percentage of preferably 2% by mass or more and 50% by mass or less, and more preferably 2% by mass or more and 30% by mass or less.

Furthermore, the Si/SiO/C complex may be formed from a mixture of elemental silicon, a silicon oxide and a carbon material, and can be prepared also by mixing elemental silicon, a silicon oxide and a carbon material by using a mechanical milling. For example, the Si/SiO/C complex can be obtained by mixing elemental silicon, a silicon oxide and a carbon material all in the form of particles. The average particle size of the elemental silicon may be set, for example, to be smaller than the average particle size of the carbon material and the average particle size of the silicon oxide. In this manner, the elemental silicon, which changes largely in the volume upon the charge/discharge cycle, has a relatively smaller particle size, and the carbon material and the silicon oxide, which changes a little in the volume, have relatively larger particle sizes. Therefore, generation of dendrite and particle size reduction of an alloy can be more effectively inhibited.

Besides, the average particle size of the elemental silicon can be, for example, 20 µm or less and preferably 15 µm or less. Besides, the average particle size of the silicon oxide is preferably equal to or smaller than ½ of the average particle size of the carbon material, and the average particle size of the elemental silicon is preferably equal to or smaller than ½ of the average particle size of the silicon oxide. Furthermore, it is more preferable that the average particle size of the silicon oxide is equal to or smaller than ½ of the average particle size of the carbon material and that the average particle size of the elemental silicon is equal to or smaller than ½ of the average particle size of the silicon oxide. If the average particle sizes are controlled to fall in these ranges, the effect to relax the volume expansion can be more effectively attained, and a secondary battery excellent in balance between the energy density and the cycle life and efficiency can be obtained. More specifically, it is preferred that the average particle size of the silicon oxide is equal to or smaller than ½ of the average particle size of graphite and that the average particle size of the elemental silicon is equal to or smaller than ½ of the average particle size of the silicon oxide. Furthermore specifically, the average particle size of the elemental silicon may be, for example, 20 µm or less and is preferably 15 µm or less. Alternatively, a substance obtained by treating the surface of the Si/SiO/C complex with a silane coupling agent may be used as the negative electrode active material.

Negative Electrode Binder

The negative electrode binder is not especially limited, and polyvinylidene fluoride, a vinylidene fluoride-hexafluoropropylene copolymer, a vinylidene fluoride-tetrafluoroethylene copolymer, polytetrafluoroethylene, polypropylene, polyethylene, polyimide, polyamide-imide, various types of polyurethane or the like may be used. Among these, polyimide, and polyamide-imide are preferably used because strong adhesion can be attained by them. Further, an aqueous binder may be also used. The aqueous binder is not especially limited, and usually a water-dispersible polymer is used in a form of a latex or an emulsion. For example, an acryl-based resin emulsion, a styrene-based resin emulsion, a vinyl acetate-based polymer emulsion, a urethane-based resin emulsion or the like can be used. Among these, a water-dispersible synthesized rubber latex or emulsion is preferably used from the viewpoint of viscoelastic properties. Examples of the water-dispersible synthetic rubber latex (emulsion) include a polybutadiene rubber latex, a styrene-butadiene rubber latex, an acrylonitrile-butadiene rubber latex, a (meth)acrylate-butadiene rubber latex, and a chloroprene rubber latex. From the viewpoint of resistance to an electrolyte solution, a styrene-butadiene rubber latex (SBR latex) is preferably used. These binders may be used singly, or two or more of them may be used in combination. The amount of the negative electrode binder to be used is preferably 2 to 10 parts by mass based on 100 parts by mass of the negative electrode active material from the viewpoint of a trade-off relationship between "sufficient binding force" and "high energy".

Negative Electrode Thickener

A thickener may also be used in order to facilitate to prepare a negative electrode slurry. Examples of the thickener include carboxymethyl cellulose (including a lithium salt, sodium salt and potassium salt neutralized with an alkali), polyethylene oxide, polypropylene oxide, hydroxyethyl cellulose, hydroxypropyl cellulose, carboxymethyl hydroxyethyl cellulose, polyvinyl alcohol, polyacrylamide, hydroxyethyl polyacrylate, ammonium polyacrylate, polyacrylic acid (including a lithium salt, a sodium salt and a potassium salt neutralized with an alkali). These thickeners may be used singly, or two or more of them may be used in combination. The ratio of the thickener in the negative electrode slurry is preferably 0.1 to 5% by mass.

Negative Electrode Electrically-Conductive Assistant

To the negative electrode, an electrically-conductive assistant may be added for the purpose of lowering the impedance. Examples of the electrically-conductive assistant include electrically-conductive carbon blacks such as acetylene black and Ketjen black; graphite powders such as artificial graphite and natural graphite; carbon fibers such as a vapor phase-grown carbon fiber and a carbon nanotube; and electrically-conductive polymers such as polyaniline, polypyrrole, polythiophene, polyacetylene and polyacene.

Negative Electrode Surfactant

In the case that water is used as the dispersion solvent, a nonionic surfactant may be used for the purpose of improving the dispersibility of carbon particles in the slurry. The nonionic surfactant is not particularly limited, and a polyoxyalkylene alkyl ether may be preferably used. The polyoxyalkylene alkyl ether is represented by a formula: R—O-(AO)$_n$H (wherein, R represents alkyl group; A represents alkylene group; and n represents a natural number). Here, the number of carbon atoms in the alkyl group represented by R, the number of carbon atoms in the alkylene group represented by A and the degree of polymerization of the alkyleneoxy group (AO) represented by n are not especially limited. The polyoxyalkylene alkyl ether may be a mixture of a plurality of polyoxyalkylene alkyl ethers which are different to each other in at least one of the number of carbon atoms in the alkyl group represented by R, the number of carbon atoms in the alkylene group represented by A and the degree of polymerization of the alkyleneoxy group (AO) represented by the reference sign n.

Coating-Forming Additive

The coating-forming additive contained in the negative electrode in the present invention is at least one selected from the group consisting of a compound represented by formula (1) and a compound represented by formula (2). It is noted that, in the present invention, "containing" a coating-forming additive means that an oxetane compound as a monomer may have been polymerized via reaction.

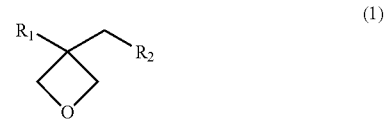

(1)

wherein $R_1$ represents —H or alkyl group having 1 to 5 carbon atoms; and $R_2$ represents —OH, —O—X, —O—C(=O)X, —O—C(=O)—O—X, —O—C(=O)—NH—X, —O—P(=O)(OC$_a$H$_{2a+1}$)$_2$, —O—P(OC$_b$H$_{2b+1}$)$_2$, or —O—P(=O)(OC$_c$H$_{2c+1}$)(C$_d$H$_{2d+1}$), and wherein X represents alkyl group, alkenyl group, or phenyl group; and a, b, c and d each independently represent an integer of 1 to 10;

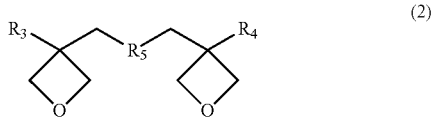

(2)

wherein $R_3$ and $R_4$ each independently represent —H, —CH$_3$, or —C$_2$H$_5$; and $R_5$ represents —O—, —O—Y—O—, —O—C(=O)—Y—C(=O)—O—, —O—C(=O)—NH—Y—NH—C(=O)—O—, —(O—C$_6$H$_4$)$_q$— (q is an integer of 1 to 5), —(O—CH$_2$—C$_6$H$_4$—CH$_2$)—O— (n is an integer of 1 to 5), —O—P(=O)(OC$_s$H$_{2s+1}$)—O— (s is an integer of 1 to 10), —O—P(OC$_m$H$_{2m+1}$)—O— (m is an integer of 1 to 10), —O—P(=O)(C$_t$H$_{2t+1}$)—O— (t is an integer of 1 to 10) or —O—P(—C$_6$H$_5$)—O—, and wherein —Y— represents —C$_p$H$_{2p}$— (p is an integer of 1 to 10), cyclohexylene group, alkenylene group, —(C$_6$H$_4$)$_r$— (r is an integer of 1 to 5), —(C$_u$H$_{2u}$—O)$_x$— (u is an integer of 1 to 10, and x is an integer of 1 to 5), —(CH$_2$—CH$_2$—O)$_k$—CH$_2$—CH$_2$— (k is an integer of 0 to 3) or —C(=O)—.

It is noted that, in the present specification, "—C$_6$H$_4$—" represents phenylene group and "—C$_6$H$_5$" represents phenyl group.

In the monofunctional oxetane compound represented by formula (1), $R_1$ is —H or alkyl group having 1 to 5 carbon atoms, preferably —H, —CH$_3$, or —C$_2$H$_5$, and more preferably —CH$_3$ or —C$_2$H$_5$.

In formula (1), $R_2$ represents —OH, —O—X, —O—C(=O)X, —O—C(=O)—O—X, —O—C(=O)—NH—X, —O—P(=O)(OC$_a$H$_{2a+1}$)$_2$, —O—P—(OC$_b$H$_{2b+1}$)$_2$, or —O—P(=O)(OC$_c$H$_{2c+1}$)(C$_d$H$_{2d+1}$). Here, —X represents alkyl group, alkenyl group or phenyl group, and a, b, c and d each independently represent an integer of 1 to 10. Thus, $R_2$ is a group having —OH group or otherwise alkyl group, alkenyl group or phenyl group having an ether linkage, an ester linkage, a carbonate linkage or a urethane linkage; phosphate group; or phosphite group. Alkyl group and alkenyl group may be linear or branched.

In formula (1), in the case that $R_2$ is —O—X, —O—C(=O)X, —O—C(=O)—O—X or —O—C(=O)—NH—X, —X at each substituent represents alkyl group, alkenyl group or phenyl group.

In formula (1), in the case that —X is alkyl group, —X is preferably alkyl group having 1 to 8 carbon atoms, and examples thereof include methyl group, ethyl group, propyl group, isopropyl group, butyl group, isobutyl group, t-butyl group, pentyl group, isopentyl group, hexyl group, isohexyl group, 3-methylpentyl group, 2,3-dimethylbutyl group, 2,2-dimethylbutyl group, heptyl group, 2-methylhexyl group, 3-methylhexyl group, 2,3-dimethylpentyl group, 2,4-dimethylpentyl group, 2,2-dimethylpentyl group, 3,3-dimethylpentyl group, 3-ethylpentyl group, 2,2,3-trimethylbutyl group, octyl group, 2-methylheptyl group, 3-methylheptyl group, 4-methylheptyl group, 2-ethylhexyl group, 3-ethylhexyl group, 2,2-dimethylhexyl group, 2,3-dimethylhexyl group, 2,4-dimethylhexyl group, 2,5-dimethylhexyl group, 3,3-dimethylhexyl group, 3,4-dimethylhexyl group, 3-ethyl-2-methylpentyl group, 3-ethyl-3-methylpentyl group, 2,2,3-trimethylpentyl group, 2,2,4-trimethylpentyl group, 2,3,3-trimethylpentyl group, 2,3,4-trimethylpentyl group and 2,2,3,3-tetramethylbutyl group.

In formula (1), in the case that —X is alkenyl group, —X is preferably alkenyl group having 2 to 5 carbon atoms, and examples thereof include vinyl group, allyl group, 1-propenyl group, isopropenyl group, 3-butenyl group, 1-methyl-1-propenyl group, 1-methyl-2-propenyl group, 2-methyl-2-propenyl group, 1-butenyl group, 2-butenyl group and 1-pentenyl group.

In the case that $R_2$ is —O—X, —X is preferably methyl group, ethyl group, propyl group, butyl group, 2-methylhexyl group, 2-ethylheptyl group, 2-ethylhexyl group, vinyl group or allyl group.

In the case that $R_2$ is —O—C(=O)X, —X is preferably methyl group, ethyl group, propyl group, butyl group, vinyl group or allyl group.

In the case that $R_2$ is —O—C(=O)—O—X, —X is preferably methyl group, ethyl group, propyl group, butyl group, vinyl group or allyl group.

In the case that $R_2$ is —O—C(=O)—NH—X, —X is preferably methyl group, ethyl group, propyl group, butyl group, vinyl group or allyl group.

In the case that $R_2$ is —O—P(=O)(OC$_a$H$_{2a+1}$)$_2$, a in two —OC$_a$H$_{2a+1}$ present therein each independently represent an integer of 1 to 10, and preferably an integer of 1 to 5. In addition, two —OC$_a$H$_{2a+1}$ groups present therein are more preferably the same as each other.

In the case that $R_2$ is —O—P(OC$_b$H$_{2b+1}$)$_2$, b in two —OC$_b$H$_{2b+1}$ present therein each independently represent an integer of 1 to 10, and preferably an integer of 1 to 5. In addition, two —OC$_b$H$_{2b+1}$ present therein are more preferably the same as each other.

In the case that $R_2$ is —O—P(=O)(OC$_c$H$_{2c+1}$)(C$_d$H$_{2d+1}$), c and d each independently represent an integer of 1 to 10, c is preferably an integer of 1 to 5, and d is preferably an integer of 1 to 5.

In formula (1), $R_2$ is more preferably —OH, methoxy group, ethoxy group or —O—X (—X represents 2-ethylhexyl group).

Examples of the compound represented by formula (1) include 3-methyl-3-oxetane methanol, 3-ethyl-3-oxetane methanol, 3-methyl-3-(methoxymethyl)oxetane, 3-methyl-3-(ethoxymethyl)oxetane, 3-methyl-3-(propoxymethyl)oxetane, 3-methyl-3-(butoxymethyl)oxetane, 3-ethyl-3-(methoxymethyl)oxetane, 3-ethyl-3-(ethoxymethyl)oxetane, 3-ethyl-3-(propoxymethyl)oxetane, 3-ethyl-3-(butoxymethyl)oxetane, 3-methyl-3-(vinyloxymethyl)oxetane, 3-ethyl-3-(vinyloxymethyl)oxetane, 3-methyl-3-(2-ethylhexyloxymethyl)oxetane and 3-ethyl-3-(2-ethylhexyloxymethyl)oxetane.

In the difunctional oxetane compound represented by formula (2), $R_3$ and $R_4$ each independently represent —H, —CH$_3$, or —C$_2$H$_5$, and preferably —CH$_3$ or —C$_2$H$_5$. In addition, $R_3$ and $R_4$ are more preferably the same.

In formula (2), $R_5$ represents —O—, —O—Y—O—, —O—C(=O)—Y—C(=O)—O—, —O—C(=O)—NH—Y—NH—C(=O)—O—, —(O—C$_6$H$_4$)$_q$— (q is an integer of 1 to 5), —(O—CH$_2$—C$_6$H$_4$—CH$_2$)$_n$—O— (n is an integer of 1 to 5), —O—P(=O)(OC$_s$H$_{2s+1}$)—O— (s is an integer of 1 to 10), —O—P(OC$_m$H$_{2m+1}$)—O— (m is an integer of 1 to 10), —O—P(=O)(C$_t$H$_{2t+1}$)—O— (t is an integer of 1 to 10) or —O—P(—C$_6$H$_5$)—O—. Here, —Y— represents —C$_p$H$_{2p}$— (p is an integer of 1 to 10), cyclohexylene group, alkenylene group, —(C$_6$H$_4$)$_r$— (r is an integer of 1 to 5), —(C$_u$H$_{2u}$—O)$_x$— (u represents an integer of 1 to 10, and x represents an integer of 1 to 5), —(CH$_2$—CH$_2$—O)$_k$—CH$_2$—CH$_2$— (k is an integer of 0 to 3) or —C(=O)—. Thus, $R_5$ is a divalent group having —O— (oxygen) or otherwise alkylene group, alkenylene group or phenylene group having an ether linkage, an ester linkage, a carbonate linkage or a urethane linkage; an oligomeric phenyl ether structure; a phosphate structure; a phosphite structure; a phosphonate structure or the like.

In formula (2), in the case that $R_5$ is —O—Y—O—, —O—C(=O)—Y—C(=O)—O—, or —O—C(=O)—NH—Y—NH—C(=O)—O—, —Y— at each substituent represents —$C_pH_{2p}$— (p is an integer of 1 to 10), cyclohexylene group, alkenylene group, —$(C_6H_4)_r$— (r is an integer of 1 to 5), —$(C_uH_{2u}$—O$)_x$— (u represents an integer of 1 to 10, and x represents an integer of 1 to 5), —$(CH_2$—$CH_2$—O$)_k$—$CH_2$—$CH_2$— (k is an integer of 0 to 3) or —C(=O)—.

In formula (2), in the case that —Y— is —$C_pH_{2p}$—, p is an integer of 1 to 10, preferably an integer of 1 to 5, and examples thereof include methylene group, ethylene group, propylene group, butylene group and pentylene group.

In formula (2), in the case that —Y— is alkenylene group, —Y— is preferably alkenylene group having 2 to 5 carbon atoms, and examples thereof include vinylene group, 1-methylvinylene group, propenylene group, 1-butenylene group, 2-butenylene group, 1-pentenylene group and 2-pentenylene group.

In formula (2), in the case that —Y— is —$(C_6H_4)_r$—, r is an integer of 1 to 5, and preferably an integer of 1 to 3.

In formula (2), in the case that —Y— is —$(C_uH_{2u}$—O$)_x$—, u is an integer of 1 to 10, preferably an integer of 1 to 5, and x is an integer of 1 to 5, and preferably an integer of 1 to 3.

In formula (2), in the case that $R_5$ is —O—Y—O—, —Y— is preferably methylene group, propylene group, —$(CH_2$—$CH_2$—O$)_k$—$CH_2$—$CH_2$— (k is an integer of 0 to 3) or —C(=O)—.

In formula (2), in the case that $R_5$ is —O—C(=O)—Y—C(=O)—O—, —Y— is preferably methylene group, ethylene group, cyclohexylene group or —$C_6H_4$—.

In formula (2), in the case that $R_5$ is —O—C(=O)—NH—Y—NH—C(=O)—O—, —Y— is preferably methylene group or ethylene group.

In formula (2), in the case that $R_5$ is —(O—$C_6H_4)_q$—, q is an integer of 1 to 5, and preferably 1 to 3.

In formula (2), in the case that $R_5$ is —(O—$CH_2$—$C_6H_4$—$CH_2)_n$—O—, n is an integer of 1 to 5, and preferably 1 to 3.

In formula (2), in the case that $R_5$ is —O—P(=O)(OC$_sH_{2s+1}$)—O—, s is an integer of 1 to 10, and preferably 1 to 5.

In formula (2), in the case that $R_5$ is —O—P(OC$_mH_{2m+1}$)—O—, m represents an integer of 1 to 10, and preferably an integer of 1 to 5.

In formula (2), in the case that $R_5$ is —O—P(=O)(C$_tH_{2t+1}$)—O—, t is an integer of 1 to 10, and preferably 1 to 5.

In formula (2), $R_5$ is more preferably —O—, —O—C(=O)—O— or —(O—$CH_2$—$C_6H_4$—$CH_2)_n$—O— (n is an integer of 1 to 5) or —O—$(CH_2$—$CH_2$—O$)_k$—$CH_2$—$CH_2$—O— (k is an integer of 0 to 3).

Examples of the compound represented by formula (2) include 3-ethyl-3{[(3-ethyloxetane-3-yl)methoxy]methyl}oxetane, bis(3-ethyl-3-oxetanylmethoxymethyl)methane, 1,2-bis(3-ethyl-3-oxetanylmethoxymethyl)ethane, bis(3-ethyl-3-oxetanylmethoxymethyl)propane, bis(3-ethyl-3-oxetanylmethoxymethyl)butane, ethylene glycol bis(3-ethyl-3-oxetanylmethyl)ether, triethylene glycol bis(3-ethyl-3-oxetanylmethyl)ether, tetraethylene glycol bis(3-ethyl-3-oxetanylmethyl)ether, dioxetane carbonate, xylylene bisoxetane, terephthalic acid=bis[(3-ethyloxetane-3-yl)methyl] represented by the following formula (8), cyclohexyl dicarboxylic acid bis[(3-ethyloxetane-3-yl)methyl] represented by the following formula (9), 1,4-bis(3-ethyl-3-oxetanylmethoxymethyl)benzene, 4,4'-bis(3-ethyl-3-oxetanylmethoxymethyl)biphenyl, bis[(3-ethyloxetane-3-yl)methyl]phenyl phosphite, isophthalic acid=bis[(3-ethyloxetane-3-yl)methyl] and phthalic acid=bis[(3-ethyloxetane-3-yl)methyl].

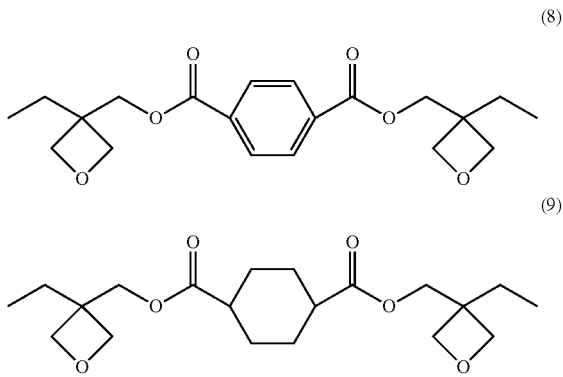

The oxetane compound represented by formula (1) or formula (2) can be synthesized via a common chemical reaction. For example, the oxetane compound can be synthesized by using an oxetane alcohol as a raw material via a reaction with hydroxyl group in the oxetane alcohol such as a urethanization reaction, an etherification reaction, an esterification reaction and a carbonation reaction.

The oxetane compound may be used singly, or two or more oxetane compounds may be used in combination. The oxetane compound is cationically ring-opening polymerized by using an acid in the electrolyte solution as an initiator to form a polymer coating. In a negative electrode prepared by adding the oxetane compound to a negative electrode slurry, the oxetane compound in the negative electrode is rapidly polymerized through contacting with the electrolyte solution to form a polymer-like coating on the surface of the negative electrode, and therefore the decomposition reaction of the electrolyte solution can be suppressed to provide a battery excellent in a cycle characteristic. For example, in the case that water is used as a dispersion solvent in preparing a slurry, 3-methyl-3-oxetane methanol or 3-ethyl-3-oxetane methanol, each of which being a water-soluble oxetane compound, is preferably used among the oxetane compounds. Further is preferably used an oxetane having a functional group such as carbonate group and phosphate group, each of which has a high affinity for the electrolyte solution, an oxetane having phenyl group, which has a high affinity for the surface of the negative electrode, or an oxetane having ethylene glycol group, triethylene glycol group or tetraethylene glycol group (i.e., a group represented by —O—$(CH_2$—$CH_2$—O$)_k$—$CH_2$—$CH_2$—O— (k is an integer of 0 to 3)), each of which exhibits lithium ion conductivity. The difunctional oxetane compound represented by formula (2) is preferably used from the viewpoint of a high coating effect on the surface of the negative electrode.

The coating-forming additive exemplified in this embodiment may be used regardless of the solubility in the dispersion solvent for a slurry. The coating-forming additive is dispersed in the slurry, and after, application and drying thereof, the coating-forming additive is preferably attached to the surface, and more preferably attached only to the surface of a negative electrode active material. On the other hand, too much amount of the coating-forming additive provides a thick coating, resulting in the increase of the internal resistance of the electrode. This reduces lithium ion conductivity and electron conductivity in the electrode, and as a result battery characteristics are deteriorated. Accordingly, the amount of the coating-forming additive added is preferably 0.001 to 5.0% by mass, more preferably 0.01 to 2.0% by mass, and more preferably 0.01 to 0.3% by mass based on the mass of the negative electrode active material. The smaller the amount to be added is, the more advantageous with respect to cost it is.

Negative Electrode Collector

As the material of the negative electrode collector, any of known materials may be arbitrarily used, and for example, a metal material such as copper, nickel or SUS is used. In particular, copper is particularly preferably used from the viewpoint of workability and cost. Besides, the collector is preferably precedently subjected to a surface-roughening treatment. Furthermore, the shape of the collector is arbitrary, and may be a foil shape, a plate shape, a mesh shape or the like. Alternatively, a perforated collector of an expanded metal or a punching metal may be used. In addition, in the case that a thin film is used as the collector, the preferable thickness and shape are also arbitrary.

Method of Preparing a Negative Electrode

The negative electrode may be prepared, for example, by forming on the negative electrode collector, a negative electrode active material layer containing the negative electrode active material, the negative electrode binder and the coating-forming additive, and in addition optionally containing the negative electrode thickener, the surfactant or the like. Examples of the method for forming a negative electrode active material layer include a doctor blade method, a the coater method, a CVD method, or a sputtering method. Alternatively, after precedently forming the negative electrode active material layer, a thin film of aluminum, nickel or an alloy of them may be formed thereon by vapor deposition, sputtering or the like to be used as the negative electrode collector. Especially, a method in which a slurry is prepared by mixing the negative electrode active material, the negative electrode binder, the negative electrode thickener, the coating-forming additive, the surfactant and the like into the dispersion solvent, applied to a collector, and thereafter heat-dried is preferred because it enables an inexpensive production. For the purpose of preventing the attachment of the coating-forming additive to the binder, it is preferable to disperse the negative electrode active material, the negative electrode thickener, the coating-forming additive and the surfactant, and thereafter finally add the negative electrode binder. The heat-drying temperature after applying the slurry to the negative electrode collector is preferably 50° C. or higher and 140° C. or lower, and more preferably 80° C. or higher and 120° C. or lower. The dispersion solvent is preferably NMP or water, and more preferably water.

In the present embodiment, a negative electrode in which the coating-forming additive is contained in advance can be obtained by adding the oxetane compound as the coating-forming additive to the negative electrode slurry, applying and drying the resultant in producing a lithium ion secondary battery. In the present embodiment, since the coating-forming additive is not added to the nonaqueous electrolyte solution and the coating formed on the surface of the negative electrode is a polymer of the oxetane compound, the coating-forming additive does not elute into the non-aqueous electrolyte solution. Due to this, the lithium ion secondary battery according to the present embodiment has advantages: for example, the viscosity of the electrolyte solution is not increased and therefore the ion conductivity is not reduced; the coating-forming additive can be used even in the case that it is incompatible with the electrolyte solution; and the coating-forming additive does not attach to the positive electrode and therefore the resistance of the positive electrode is not increased. Further, in the case that the amount of the additive to be added is within the range according to the present invention, the dispersed state of the slurry is not disturbed, which enables to prepare a uniform negative electrode. In addition, in the case that the amount of the additive to be added is within the range according to the present invention, the additive does not attach in a large amount to the binder, and therefore the binding effect of the binder is not reduced and the adhesion properties between the negative electrode and the collector are not deteriorated. Accordingly, since the degradation of battery characteristics such as the lowering of a cycle of the battery and swelling due to the generation of an inner gas can be suppressed and the degradation of the storage characteristic of the electrolyte solution can also be suppressed, an excellent nonaqueous electrolyte solution secondary battery can be provided.

[2] Positive Electrode

Positive Electrode Active Material Layer

A positive electrode active material layer contains a positive electrode active material, and has a structure in which the positive electrode active material is bound on a positive electrode collector with a positive electrode binder. The positive electrode active material desorbs lithium ions into an electrolyte solution at the time of charge and absorbs lithium from the electrolyte solution at the time of discharge, and examples thereof include lithium manganate having a layered structure, such as $LiMnO_2$ or $Li_xMn_2O_4$ ($0<x<2$), or lithium manganate having a spinel structure; $LiCoO_2$, $LiNiO_2$ or a substance in which a part of a transition metal of these is substituted with another metal; a lithium transition metal oxide in which a specific transition metal occupies less than a half of the whole structure, such as $LiNi_{1/3}Co_{1/3}Mn_{1/3}O_2$; and such a lithium transition metal oxide containing Li more excessively than in a stoichiometric composition. In particular, $Li_\alpha Ni_\beta Co_\gamma Al_\delta O_2$ ($1 \le \alpha \le 1.2$, $\beta+\gamma+\delta=1$, $\beta \ge 0.7$ and $\gamma \le 0.2$), or $Li_\alpha Ni_\beta Co_\gamma Mn_\delta O_2$ ($1 \le \alpha \le 1.2$, $\beta+\gamma+\delta=1$, $\beta \ge 0.6$ and $\gamma \le 0.2$) is preferable. One of these positive electrode active materials may be singly used, or two or more of them may be used in combination.

As the positive electrode binder which binds the above positive electrode active material to integrate together, specifically, any of those mentioned above as the negative electrode binder may be used. From the viewpoint of multiple use and low cost, polyvinylidene fluoride is preferable as the positive electrode binder. The amount of the positive electrode binder to be used is preferably 2 to 10 parts by mass based on 100 parts by mass of the positive electrode active material. In the case that the content of the positive electrode binder is 2 parts by mass or more, the adhesion properties between the active materials or between the active material and the collector are improved to bring the better cycle characteristic, and in the case of 10 parts by mass or less, the active material ratio is increased to improve the positive electrode capacity.

To the above positive electrode active material layer, an electrically-conductive assistant may be added for purpose of lowering the impedance of the positive electrode active material. As the electrically-conductive assistant may be used carbonaceous fine particles such as graphite, carbon black and acetylene black.

Positive Electrode Binder

The positive electrode binder is not especially limited, and for example, polyvinylidene fluoride, a vinylidene fluoride-hexafluoropropylene copolymer, a vinylidene fluoride-tetrafluoroethylene copolymer, a styrene-butadiene copolymer rubber, polytetrafluoroethylene, polypropylene, polyethylene, polyimide, polyamide-imide or the like may be used. Among these, polyimide, polyamide-imide, polyacrylic acids (including a lithium salt, a sodium salt and a potassium salt neutralized with an alkali), and carboxymethyl celluloses (including a lithium salt, a sodium salt and a potassium salt neutralized with an alkali) are preferably used because strong adhesion can be attained by them. The amount of the positive electrode binder to be used is preferably 2 to 10 parts by mass based on 100 parts by mass of the negative electrode active material from the viewpoint of a trade-off relationship between "sufficient binding force" and "high energy".

Positive Electrode Collector

As the positive electrode collector may be any of those as long as it supports the positive electrode active material layer containing the positive electrode active material to be integrated together with a binder and has electrical conductivity to enable connection to an external terminal, and specifically, any of those mentioned above as the negative electrode collector may be used.

Method for Producing Positive Electrode

An example of a method for producing a positive electrode is not especially limited, and is, for example, a method in which only a powder of a surface-treated Mn based positive electrode, or a powder of a surface-treated Mn based positive electrode and a powder of a lithium-nickel complex oxide is/are mixed with an electrically-conductive assistant and a binder in an appropriate dispersion medium which can dissolve the binder (a slurry method); the slurry is then applied to a collector such as an aluminum foil; the solvent is dried out; and the resultant is thereafter compressed to form a film by pressing or the like. It is noted that the electrically-conductive assistant is not especially limited and any one generally used such as carbon black, acetylene black, natural graphite, artificial graphite and carbon fiber may be used.

[3] Electrolyte Solution

The electrolyte solution may contain as an aprotic solvent one or more solvents selected from the group consisting of cyclic carbonates, chain carbonates, aliphatic carboxylates, γ-lactones, cyclic ethers and chain ethers and fluorine derivatives thereof. Specifically, for example, among propylene carbonate (PC), ethylene carbonate (EC), cyclic carbonates such as butylene carbonate (BC), chain carbonates such as dimethyl carbonate (DMC), diethyl carbonate (DEC), ethyl methyl carbonate (EMC), dipropyl carbonate (DPC), aliphatic carboxylates such as methyl formate, methyl acetate, ethyl propionate, γ-lactones such as γ-butyrolactone, chain ethers such as 1,2-diethoxyethane (DEE) and ethoxymethoxyethane (EME), cyclic ethers such as tetrahydrofuran and 2-methyltetrahydrofuran, dimethylsulfoxide, 1,3-dioxolane, form amide, acetamide, dimethylformamide, acetonitrile, propionitrile, nitromethane, ethyl monoglyme, phosphoric acid triesters, trimethoxymethane, 1,3-dimethyl-2-imidazolidinone, 3-methyl-2-oxazolidinone, propylene carbonate derivatives, tetrahydrofuran derivatives, ethyl ether, and N-methylpyrrolidone, one of them may be singly used, or two or more of them may be used in a mixture.

In the electrolyte solution for a secondary battery in the present embodiment, a lithium salt can be further contained as an electrolyte. In this manner, a lithium ion can be a transferring substance, and thereby battery characteristics can be improved. As a lithium salt, one or more substances selected from, for example, a lithium imide salt, $LiPF_6$, $LiBF_4$, $LiAsF_6$, $LiSbF_6$, $LiClO_4$, $LiAlCl_4$ and $LiN(C_nF_{2n+1}SO_2)(C_mF_{2m+1}SO_2)$ (each of n and m is a natural number) may be contained. Further, it is particularly preferable to use $LiPF_6$ or $LiBF_4$. By using them, the electric conductivity of a lithium salt can be enhanced and the cycle characteristic of a secondary battery can be further improved.

Further, in the present embodiment, it is believed that an acid generated by the slight decomposition of the lithium salt in the electrolyte solution can cause a ring-opening polymerization reaction of the oxetane compound in the negative electrode to form a polymer coating. Accordingly, in order to form a coating, it is preferable to perform charging/discharging, for example, 10 minutes to 1 day after the contact between the electrolyte solution and the electrode (impregnation of the electrode with the electrolyte solution or injection of the electrolyte solution into the cell). The reaction time varies depending on the type and concentration of the oxetane compound, the type and concentration of the lithium salt, the reaction temperature or the like. It is noted, for example, Japanese Patent Laid-Open No. 2001-155767 describes adding the oxetane compound to the electrolyte solution, however, in this case, a polymerization reaction of the oxetane compound occurs in the electrolyte solution to make the electrolyte solution gel-like, and accordingly it is not preferable to add the oxetane compound to the electrolyte solution. Alternatively, in the case that the additive is contained in the nonaqueous electrolyte solution, the additive remains in the electrolyte solution and may cause problems such as the attachment of the additive on the surface of the positive electrode and the increase of the viscosity of the electrolyte solution.

[4] Separator

A separator is not especially limited, and a porous film or a nonwoven fabric of polypropylene, polyethylene or the like can be used. Alternatively, a separator obtained by laminating such a material may be used.

[5] Outer Package

An outer package is not especially limited, and for example, a laminated film may be used. Any laminated film can be appropriately selected to be used as long as it is stable to the electrolyte solution and has a sufficient steam barrier property. As the laminated film used as the outer package, for example, a laminated film of aluminum, silica, polypropylene coated with alumina, or polyethylene can be used. In particular, from the viewpoint of inhibiting the volume expansion, an aluminum laminated film is preferably used.

In a secondary battery using a laminated film as the outer package, the strain of an electrode element caused when a gas is generated is extremely large as compared with that caused in a secondary battery using a metal can as the outer package. This is because the laminated film is more easily deformed by the internal pressure of the secondary battery than the metal can. Furthermore, when sealing a secondary battery using a laminated film as the outer package, the pressure within the battery is generally decreased to be lower than the atmospheric pressure, and hence, there remains no spare room within the battery. Therefore, the generation of a gas immediately leads to the volume change of the battery or the deformation of an electrode element in some cases.

In a secondary battery of the present embodiment, these problems can be overcome. As a result, a laminated type lithium ion secondary battery that is inexpensive and shows an excellent degree of freedom in design of cell capacity by changing the number of laminated layers can be provided. A typical example of the layered structure of the laminated film is a structure in which a metal thin film layer and a heat fusion-bondable resin layer are laminated. Another typical example of the layered structure of the laminated film is a structure in which a protective layer of a film of polyester such as polyethylene terephthalate or nylon is further laminated on a surface of the metal thin film layer opposite to the heat fusion-bondable resin layer. When sealing a battery element, the battery element is surrounded with the heat fusion-bondable resin layer opposed. As the metal thin film layer, for example, a foil of Al, Ti, Ti alloy, Fe, stainless steel, Mg alloy or the like having a thickness of 10 to 100 µm is used. A resin used in the heat fusion-bondable resin layer is not especially limited as long as it is capable of fusion-bonding with heat. For example, polypropylene, polyethylene, an acid-modified product of these resins, polyphenylene sulfide, polyester such as polyethylene terephthalate, polyamide, an ethylene-vinyl acetate copolymer, or an ionomer resin obtained by intermolecular bonding, with metal ions, of an ethylene-methacrylic acid copolymer or an ethylene-acrylic acid copolymer is used as the heat fusion-bondable resin layer. The thickness of the heat fusion-bondable resin layer is preferably 10 to 200 µm, and more preferably 30 to 100 µm.

[6] Battery Structure

The structure of the secondary battery is not especially limited, and for example, a laminated type structure in which an electrode element including a positive electrode and a negative electrode disposed so as to face each other, and an electrolyte solution are housed in an outer package may be employed. FIG. 1 is a schematic cross-sectional view illustrating the structure of an electrode element of a laminated type secondary battery. In this electrode element, a plurality of positive electrodes 1 and a plurality of negative electrode 3 both having a planar structure are alternately stacked with a separator 2 sandwiched therebetween. Positive electrode collectors 1b of the respective positive electrodes 1 are welded to one another in end portions not covered with a positive electrode active material layer 1a so as to be electrically connected to one another, and a positive electrode terminal 4 is further welded to the welded portion among them. Negative electrode collectors 3b of the respective negative electrodes 3 are welded to one another in end portions not covered with a negative electrode active material layer 3a so as to be electrically connected to one another, and a negative electrode terminal 6 is further welded to the welded portion among them. Further, the positive electrode terminal 4 and the negative electrode terminal 6 are welded to a positive electrode tab 5 and a negative electrode tab 7, respectively. In the electrode element having such a planar layered structure, no portion has small R (like a portion close to a core of a winding structure), and therefore, such an electrode element has an advantage that it is less harmfully affected by the volume change of the electrode caused through the charge/discharge cycle as compared with an electrode element having a winding structure. In other words, it is effectively used as an electrode element using an active material with which the volume expansion is liable to occur. On the other hand, since an electrode is bent in an electrode element having a winding structure, the structure is easily warped if the volume change is caused. In particular, if a negative electrode active material largely changed in the volume through the charge/discharge cycle, such as a silicon oxide, is used, the capacity is largely lowered through the charge/discharge cycle in a secondary battery using an electrode element having a winding structure.

In the electrode element having a planar layered structure, however, if a gas is generated between the electrodes, there arises a problem that the generated gas is liable to stay between the electrodes. This is for the following reason: In the electrode element having a winding structure, tension is applied to the electrodes and hence a distance between the electrodes is difficult to increase, but in the electrode element having a layered structure, a distance between the electrodes is easily increased. If an aluminum laminated film is used as the outer package, this problem becomes particularly conspicuous.

The present invention can solve the aforementioned problems by containing the oxetane compound in the negative electrode as the coating-forming additive, and hence, even a laminated type lithium ion secondary battery using a high-energy negative electrode can make long-life driving.

Accordingly, the secondary battery according to one embodiment of the present invention is a laminated type secondary battery containing an electrode element including a positive electrode and a negative electrode disposed so as to face each other, an electrolyte solution, and an outer package housing the electrode element and the electrolyte solution, wherein the negative electrode contains a negative electrode active material including at least one of a metal (a) alloyable with lithium and a metal oxide (b) capable of absorbing/desorbing lithium ions, and is bound to a negative electrode collector with a negative electrode binder, and the negative electrode contains the coating-forming additive. This is also effectively used in a secondary battery using an electrode element having a winding structure.

Other Embodiments of Invention

In the above embodiment, a compound commonly known as a positive electrode active material such as $LiCoO_2$ may be also used in a mixture with a positive electrode active material primarily containing a surface-treated Mn based positive electrode. In addition, an additive substance such as $Li_2CO_3$ generally used for safety or the like can be further added.

Further in the above embodiment, as an outer package of a battery may be adopted various shapes such as a rectangular type, a paper type, a laminated type, a cylindrical type and a coin type. The outer material and other constituent members are not especially limited and may be selected depending on a battery shape. As an example, a film-shaped outer package can be constituted with a film formed by laminating the aforementioned heat fusion-bondable resin film on a heat-resistant resin film such as a polyethylene terephthalate directly or via an adhesive, or a single film of a heat fusion-bondable resin film.

Further, in the present embodiment, the electrolyte solution may further contain a cyclic sulfonate having at least two sulfonyl groups and/or a compound having one or more sulfonyl groups.

Further, a plurality of the lithium ion secondary batteries described herein can be combined into a battery pack. Furthermore, the lithium ion secondary battery or the battery pack thereof described herein are best suited for a motor driving power supply and can be used for a vehicle application.

Examples

The present invention will be specifically described with reference to examples, and it is noted that the present invention is not limited to these examples.

Example 1

[Preparation of Negative Electrode]

To prepare a negative electrode sheet were mixed 20 g of carbon (natural graphite) as a negative electrode active material, 0.88 g of a carbon powder (artificial graphite powder) as an electrically-conductive material, 21 g of 1.0% by mass carboxymethyl cellulose (CMC) aqueous solution and 0.04 g (0.2% by mass relative to the carbon) of 3-ethyl-3-oxetane methanol represented by the following formula (3) (hereinafter, also referred to as "Compound (3)") as a coating-forming additive. To this mixture was added 1.0 g of 40% by mass SBR (styrene-butadiene rubber) aqueous solution, and stirred to prepare a uniform slurry. This slurry was applied to a copper foil with a thickness of 10 μm, dried at 80° C. for 20 minutes, and then further pressed to prepare a negative electrode sheet with a thickness of 100 μm.

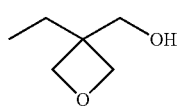

(3)

[Preparation of Coin-Type Cell]

The obtained negative electrode sheet was punched into a disk with a diameter of 12 mm, which was soaked in an electrolyte solution to fill the voids in the electrode with the electrolyte solution. As the electrolyte solution was used an ethylene carbonate/diethyl carbonate mixed solution (mixing ratio 3:7) containing 1.0 mol/L of an $LiPF_6$ electrolyte salt. On the electrode impregnated with the electrolyte solution was laminated a polypropylene porous film separator impregnated with the electrolyte solution. A lithium metal disk was further laminated thereon as the counter electrode, which was placed in a coin-type battery outer package made of stainless steel, and a pressure was applied thereon with a caulking machine to prepare a sealed coin-type cell.

[Evaluation of Cell Characteristics]

Thirty minutes after the impregnation of the electrode with the electrolyte solution, Li ions were absorbed in the negative electrode to a lower limit voltage of 0 V at a constant current of 0.25 mA at 20° C., and the initial absorption capacity was defined as an initial charging capacity. Further, the above charged cell was discharged at a constant current of 0.25 mA to an upper limit voltage of 2 V, and thereafter recharged at a constant current of 0.5 mA to a lower limit voltage of 0 V. To this recharged cell, a constant current (0.5 mA, 1 mA, 1.5 mA, 2 mA, 2.5 mA) was applied for 10 seconds, and then the current value was plotted together with the voltage value after 10 seconds, and the gradient was calculated as an initial resistance value of the negative electrode. For a cycle characteristic, a cell which had been charged to a lower limit voltage of 0 V at a constant current of 0.25 mA and thereafter discharged at a constant current of 0.25 mA to an upper limit voltage of 2 V was subjected to 20 cycles of charging/discharging at a constant current and voltage at 20° C., and a cell with a capacity retention ratio of 70% or higher was determined as "○", and a cell with a capacity retention ratio of less than 70% as "x".

Example 2

The same evaluation as in Example 1 was performed except that a negative electrode was prepared by mixing 0.12 g (0.6% by mass relative to the carbon) of Compound (3) as a coating-forming additive.

Example 3

The same evaluation as in Example 1 was performed except that a negative electrode was prepared by mixing 0.34 g (1.7% by mass relative to the carbon) of Compound (3) as a coating-forming additive.

Example 4

The same evaluation as in Example 1 was performed except that a negative electrode was prepared by mixing 0.04 g (0.2% by mass relative to the carbon) of 3-ethyl-3{[(3-ethyloxetane-3-yl)methoxy]methyl}oxetane represented by the following formula (4) (hereinafter, also referred to as "Compound (4)") as a coating-forming additive.

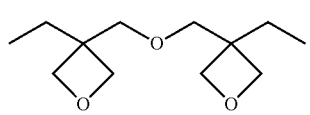

(4)

Example 5

The same evaluation as in Example 1 was performed except that a negative electrode was prepared by mixing 0.12 g (0.6% by mass relative to the carbon) of Compound (4) as a coating-forming additive.

Example 6

The same evaluation as in Example 1 was performed except that a negative electrode was prepared by mixing 0.34 g (1.7% by mass relative to the carbon) of Compound (4) as a coating-forming additive.

Example 7

The same evaluation as in Example 1 was performed except that a negative electrode was prepared by mixing 0.04 g (0.2% by mass relative to the carbon) of dioxetane carbonate represented by the following formula (5) (hereinafter, also referred to as "Compound (5)") as a coating-forming additive.

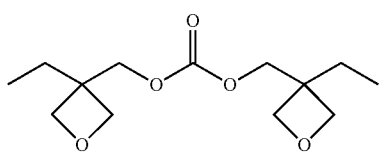

(5)

Example 8

The same evaluation as in Example 1 was performed except that a negative electrode was prepared by mixing 0.12 g (0.6% by mass relative to the carbon) of Compound (5) as a coating-forming additive.

Example 9

The same evaluation as in Example 1 was performed except that a negative electrode was prepared by mixing 0.34 g (1.7% by mass relative to the carbon) of Compound (5) as a coating-forming additive.

Example 10

The same evaluation as in Example 1 was performed except that a negative electrode was prepared by mixing 0.04 g (0.2% by mass relative to the carbon) of xylylene bisoxetane represented by the following formula (6) (hereinafter, also referred to as "Compound (6)") as a coating-forming additive.

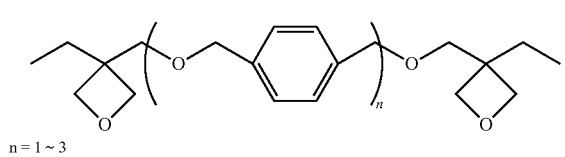

(6)

n = 1 ~ 3

Example 11

The same evaluation as in Example 1 was performed except that a negative electrode was prepared by mixing 0.12 g (0.6% by mass relative to the carbon) of Compound (6) as a coating-forming additive.

Example 12

The same evaluation as in Example 1 was performed except that a negative electrode was prepared by mixing 0.34 g (1.7% by mass relative to the carbon) of Compound (6) as a coating-forming additive.

Example 13

The same evaluation as in Example 1 was performed except that a negative electrode was prepared by mixing 0.04 g (0.2% by mass relative to the carbon) of ethylene glycol bis(3-ethyl-3-oxetanylmethyl)ether represented by the following formula (7) (hereinafter, also referred to as "Compound (7)") as a coating-forming additive.

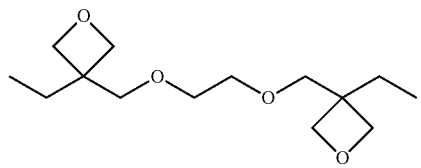

(7)

Example 14

The same evaluation as in Example 1 was performed except that a negative electrode was prepared by mixing 0.12 g (0.6% by mass relative to the carbon) of Compound (7) as a coating-forming additive.

Example 15

The same evaluation as in Example 1 was performed except that a negative electrode was prepared by mixing 0.34 g (1.7% by mass relative to the carbon) of Compound (7) as a coating-forming additive.

Comparative Example 1

The same evaluation as in Example 1 was performed except that a negative electrode was prepared without adding a coating-forming additive.

Comparative Example 2

The same evaluation as in Example 1 was performed except that a negative electrode was prepared by using Compound (3) as a coating-forming additive and changing the amount thereof to be added to 1.1 g (5.5% by mass relative to the carbon).

Comparative Example 3

The same evaluation as in Example 1 was performed except that a negative electrode was prepared by using Compound (4) as a coating-forming additive and changing the amount thereof to be added to 1.1 g (5.5% by mass relative to the carbon).

Comparative Example 4

The same evaluation as in Example 1 was performed except that a negative electrode was prepared by using Compound (5) as a coating-forming additive and changing the amount thereof to be added to 1.1 g (5.5% by mass relative to the carbon).

Comparative Example 5

The same evaluation as in Example 1 was performed except that a negative electrode was prepared by using Compound (6) as a coating-forming additive and changing the amount thereof to be added to 1.1 g (5.5% by mass relative to the carbon).

Comparative Example 6

The same evaluation as in Example 1 was performed except that a negative electrode was prepared by using Compound (7) as a coating-forming additive and changing the amount thereof to be added to 1.1 g (5.5% by mass relative to the carbon).

The evaluation results are shown in Table 1.

TABLE 1

| | Additive | Amount to be added (% by mass) | Initial charging capacity (mAh) | Initial resistance value (Ω) | Cycle characteristic |
|---|---|---|---|---|---|
| Ex. 1 | 3-ethyl-3-oxetane methanol | 0.2 | 6.6 | 64.2 | ○ |
| Ex. 2 | 3-ethyl-3-oxetane methanol | 0.6 | 5.7 | 65.1 | ○ |
| Ex. 3 | 3-ethyl-3-oxetane methanol | 1.7 | 6.1 | 63.2 | ○ |
| Ex. 4 | 3-ethyl-3{[(3-ethyloxetane-3-yl)methoxy]methyl}oxetane | 0.2 | 6.4 | 68.8 | ○ |
| Ex. 5 | 3-ethyl-3{[(3-ethyloxetane-3-yl)methoxy]methyl}oxetane | 0.6 | 6.2 | 69.6 | ○ |
| Ex. 6 | 3-ethyl-3{[(3-ethyloxetane-3-yl)methoxy]methyl}oxetane | 1.7 | 6.3 | 72.5 | ○ |
| Ex. 7 | dioxetane carbonate | 0.2 | 6.6 | 67.8 | ○ |
| Ex. 8 | dioxetane carbonate | 0.6 | 6.5 | 68.3 | ○ |
| Ex. 9 | dioxetane carbonate | 1.7 | 6.2 | 71.9 | ○ |
| Ex. 10 | xylylene bisoxetane | 0.2 | 6.3 | 65.0 | ○ |
| Ex. 11 | xylylene bisoxetane | 0.6 | 6.3 | 67.1 | ○ |
| Ex. 12 | xylylene bisoxetane | 1.7 | 6.5 | 70.2 | ○ |
| Ex. 13 | ethylene glycol bis(3-ethyl-3-oxetanylmethyl)ether | 0.2 | 6.6 | 64.7 | ○ |
| Ex. 14 | ethylene glycol bis(3-ethyl-3-oxetanylmethyl)ether | 0.6 | 6.4 | 65.4 | ○ |
| Ex. 15 | ethylene glycol bis(3-ethyl-3-oxetanylmethyl)ether | 1.7 | 6.2 | 67.1 | ○ |
| Com-Ex. 1 | none | 0 | 6.7 | 84.0 | x |
| Com-Ex. 2 | 3-ethyl-3-hydroxymethyloxetane | 5.5 | 6.1 | 91.7 | x |
| Com-Ex. 3 | 3-ethyl-3{[(3-ethyloxetane-3-yl)methoxy]methyl}oxetane | 5.5 | 6.0 | 94.5 | x |
| Com-Ex. 4 | dioxetane carbonate | 5.5 | 5.8 | 93.2 | x |
| Com-Ex. 5 | xylylene bisoxetane | 5.5 | 5.9 | 95.6 | x |
| Com-Ex. 6 | ethylene glycol bis(3-ethyl-3-oxetanylmethyl)ether | 5.5 | 5.2 | 101 | x |

(In the table, "Amount to be added" represents a mass fraction (% by mass) of an additive relative to the negative electrode active material.)
Ex. = Example
Com-Ex. = Comparative Example Table 1 shows the evaluation of initial charging capacities, initial resistance values and cycle characteristics in the case that respective additives were added to the negative electrode slurry. Internal resistance values (initial resistance values) in Examples 1 to 15 with the oxetane compound added were lower than that with no additive (Comparative Example 1). This is possibly because, in Examples 1 to 15, the oxetane compound formed a polymer coating on the surface of the negative electrode via a ring-opening polymerization reaction and suppressed the decomposition of the electrolyte solution. On the other hand, it is believed that, since no coating-forming additive was added in Comparative Example 1, the decomposition reaction of the electrolyte solution was progressed to thicken the coating, resulting in the increase of the resistance value. Meanwhile, it is believed that, since the amount of the coating-forming additive to be added in Comparative Examples 2 to 6 was larger than those in Examples, a thick polymer coating was formed to increase the resistance value. Further, after the 20 cycles of the charging/discharging test, Examples 1 to 15 resulted in a good cycle characteristic, and in contrast, Comparative Examples 1 to 6 resulted in a poor cycle characteristic. In Comparative Example 1 with no additive, a reaction between the electrolyte solution and the surface of the negative electrode occurs because a good coating is not formed on the surface of the negative electrode. Then, the decomposition product is deposited on the surface of the negative electrode, which possibly resulted in the increase of the resistance and the degradation of the cycle characteristic. On the other hand, it is believed that, because the coating on the negative electrode was too thick in Comparative Examples 2 to 6, the internal resistance of the negative electrode was increased and the cycle characteristic was degraded.

Further, preferred aspects of the present invention will be described below.

(Supplemental Item 1)

A method for producing a negative electrode for a lithium ion secondary battery comprising the steps of:

preparing a slurry comprising a negative electrode active material, at least one coating-forming additive selected from the group consisting of a compound represented by formula (1) or formula (2), a binder and a dispersion solvent, wherein an amount of the coating-forming additive is within a range of 0.001% by mass or more and 5.0% by mass or less based on an amount of the negative electrode active material; and applying the slurry to a negative electrode collector and drying the slurry.

(Supplemental Item 2)

The method for producing a negative electrode for a lithium ion secondary battery according to the Supplemental item 1, wherein, in the step of preparing a slurry, a negative electrode active material and at least one coating-forming additive selected from the group consisting of a compound represented by formula (1) or formula (2) are dispersed in a dispersion solvent, and subsequently a binder is added thereto.

(Supplemental Item 3)

The method for producing a negative electrode for a lithium ion secondary battery according to the Supplemental item 1 or 2, wherein the dispersion solvent is water.

INDUSTRIAL APPLICABILITY

The present embodiment can be utilized in, for example, all the industrial fields requiring a power supply and the industrial fields pertaining to the transportation, storage and supply of electric energy. Specifically, it can be used in, for example, power supplies for mobile equipment such as cellular phones and laptop computers; power supplies for moving/transporting media such as trains, satellites and submarines including electrically driven vehicles such as an electric vehicle, a hybrid vehicle, an electric motorbike, and an electric-assisted bike; backup power supplies for UPSs; and electricity storage facilities for storing electric power generated by photovoltaic power generation, wind power generation and the like.

REFERENCE SIGNS LIST 1 positive electrode
1a positive electrode active material layer
1b positive electrode collector
2 separator
3 negative electrode
3a negative electrode active material layer
3b negative electrode collector
4 positive electrode terminal
5 positive electrode tab
6 negative electrode terminal
7 negative electrode tab

What is claimed is:

1. A negative electrode for a lithium ion secondary battery comprising a negative electrode active material and a coating-forming additive,
wherein the negative electrode comprises the coating-forming additive in an amount within a range of 0.2% by mass or more and 1.7% by mass or less based on an amount of the negative electrode active material; and
the coating-forming additive is at least one selected from the group consisting of 3-ethyl-3-hydroxymethyloxetane, 3-ethyl-3{[(3-ethyloxetane-3-yl)methoxy]methyl}oxetane, dioxetane carbonate, xylylene bisoxetane, and ethylene glycol bis(3-ethyl-3-oxetanylmethyl)ether.

2. A lithium ion secondary battery comprising the negative electrode for a lithium ion secondary battery according to claim 1.

3. A lithium ion secondary battery having: an electrode element in which a positive electrode and a negative electrode are disposed so as to face each other, and an electrolyte solution, wherein the negative electrode is the negative electrode for a lithium ion secondary battery according to claim 1.

4. The lithium ion secondary battery according to claim 3, further comprising an outer package housing the electrode element and the electrolyte solution therein, wherein the outer package is a laminated film.

5. The lithium ion secondary battery according to claim 3, wherein the lithium ion secondary battery is a laminated type having the electrode element in which the negative electrode and the positive electrode are laminated with a separator sandwiched therebetween.

6. A battery pack comprising the lithium ion secondary battery according to claim 2.

7. A vehicle comprising, as a motor driving power supply, the lithium ion secondary battery according to claim 2.

8. A vehicle comprising, as a motor driving power supply, the battery pack according to claim 6.

9. A method for producing a negative electrode for a lithium ion secondary battery comprising the steps of:
preparing a slurry comprising a negative electrode active material, a coating-forming additive, a binder and a dispersion solvent, wherein an amount of the coating-forming additive is within a range of 0.2% by mass or more and 1.7% by mass or less based on an amount of the negative electrode active material; and
applying the slurry to a negative electrode collector and drying the slurry,
wherein the coating-forming additive is at least one selected from the group consisting of 3-ethyl-3-hydroxymethyloxetane, 3-ethyl-3{[(3-ethyloxetane-3-yl)methoxy]methyl}oxetane, dioxetane carbonate, xylylene bisoxetane, and ethylene glycol bis(3-ethyl-3-oxetanylmethyl)ether.

* * * * *